United States Patent [19]

Nagasawa et al.

[11] 4,054,648

[45] Oct. 18, 1977

[54] PROCESS FOR PREPARING A THERAPEUTIC AGENT

[75] Inventors: Taro Nagasawa; Morio Kuboyama, both of Tokyo; Joji Ono, Chiba; Minoru Saito, Komae; Tsutomu Kudo, Kawasaki; Eiji Takahashi, Narashino; Kazuyoshi Doi, Tokyo; Kazuhiro Nagata, Yokohama, all of Japan

[73] Assignee: Morinaga Milk Industry Co., Ltd., Tokyo, Japan

[21] Appl. No.: 496,814

[22] Filed: Aug. 12, 1974

[30] Foreign Application Priority Data

Aug. 30, 1973 Japan .................................. 48-96689

[51] Int. Cl.$^2$ ............................................. A61K 35/50
[52] U.S. Cl. ................................................... 424/105
[58] Field of Search .......................................... 424/105

[56] References Cited

PUBLICATIONS

Spencer et al., Cancer Research, vol. 25, No. 4, Part 2, May 1965, pp. 840-841.

Primary Examiner—Jerome D. Goldberg

Attorney, Agent, or Firm—Oblon, Fisher, Spivak, McClelland & Maier

[57] ABSTRACT

Therapeutic agents are prepared by:
- A. grinding placenta with water or diluted physiological saline to form an emulsion, and acidifying the emulsion with a mixture of aqueous acetic acid and hydrochloric acid, to 0.5 to 2.0N;
- B. heating the acidified emulsion;
- C. cooling the emulsion, removing insoluble protein by centrifugation, neutralizing the emulsion with an alkali solution, centrifuging said emulsion to remove insoluble matter and collecting a clear supernatant;
- D. concentrating the supernatant, and dialyzing the resulting concentrated liquid through a dialysis membrane, or filtrating said supernatant through a membrane filter to obtain a dialyzed fluid or filtrate;
- E. subjecting the dialyzed fluid or filtrate, after concentration to column chromatography, to obtain any one of fractions, of 0.96 – 1.82 in distribution coefficient with Sephadex G-25, of 0.35 – 1.24 with Sephadex G-15, or of 0.35 – 1.25 with Sephadex G-10; and
- F. lyophilizing the fraction.

3 Claims, 7 Drawing Figures

PROCESS FOR PREPARING A THERAPEUTIC AGENT

BACKGROUND OF THE INVENTION

1. Field of the Invention

The present invention relates to a method for preparing a therapeutic agent from placenta.

2. Description of the Prior Art

To date, many publications have been concerned with methods of extracting physiologically or pharmacologically active substances or purifying the placental extract. Some of these extracts have been reported to possess anti-ulcer or anti-cancer effects. None, of the reported prior art placental extract preparations have been shown to possess leukemia therapeutic effects.

Hieda ("REIZOTAIBAN NO SEIKAGAKU TO IRYOKOKA" or "The bio-chemistry and therapeutic effect of frozen placenta" Kinbara Shoten, 1965) reported the presence of a substance in human placenta which is effective against cirrhosis. Kumura (HIROSHIMA IGAKU 22 (12), 1136, 1969) and Saito (Clinical report 3 (7), 543, 1969) described a placenta preparation which possesses anti-ulcer effects. Also, Byong Ho Chin (Abstract of Papers of the 9th International Cancer Congress, 467 pp, 1966) communicated an anti-Ehrlich sarcoma agent and an anti-N-F sarcoma agent from human placenta.

Hieda's preparation against the cirrhosis was obtained as follows:

A fresh placenta was washed with water, permitted to stand at 2° - 4° C for several days, minced, and boiled for 60 min. The preparation was admixed with 1 N HCl in an amount of 1/5 its volume, to obtain a pH of 1.8. It was then digested with 2 g of pepsin at 38° C for 20 hours. The digested fluid was centrifuged at 3,000 r.p.m. for 15 min. to separate the supernatant from the precipitate. The supernatant was passed through an ion exchange resin to reduce its acidity to pH 4.4 - 4.6 and its volume was increased to 100 ml for every 100 g (wet weight) of placenta by the addition of water. This preparation was referred to as Solution A. The precipitate was hydrolysed with concentrated hydrochloric acid by heat treatment over a period of 10 hours. The hydrolysate was succeedingly decolorized with activated carbon, the excess volatile acid removed by evaporation on a water bath, and then subjected to secondary decolorization. The acidity of the solution was reduced with an ion exchange resin to pH 4.4 - 4.6. The volume of the eluate was made up so that every 100 g (wet weight) of placenta gave the volume of 25 ml. This preparation was referred to as Solution B. Solutions A and B were blended and the acidity of the mixture was adjusted to pH 6.1 - 6.4. Following boiling and clarification by filtration, the preparation was poured into an injection ampoule, and the solution was sterilized for use. The preparation was a transparent and yellow-colored solution, had a specific gravity of 1.0090 - 1.0132, pH of 6.1 - 6.4, showed a negative sulfosalicylic acid test and contained 78.6 - 82.3 mg/ml in dry matter. The ash, total nitrogen and amino nitrogen contents were 8.0 - 9.3 mg/ml, 9.13 - 11.21 mg/ml and 8.56 - 10.24 mg/ml respectively. The extract was claimed to possess lipotropic activity and to be capable of enhancing tissue respiration of the liver, stimulation of the thyroid gland, and basal metabolism of castrate animals. It was also reportedly useable for cirrohosis therapy, in humans and for experimental standard test animals.

Boyous Ho Chin prepared an emulsion of placenta and centrifuged it to obtain the supernatant. With addition of alcohol, a precipitation was obtained, which was subjected to fractionation by means of paper electrophoresis. The resultant fraction was dialysed against water and the dialysate or non-dialysable fraction was further subjected to precipitation with acetone. The author claimed that this precipitate possessed inhibitory effects on the growth of Ehrlich sarcoma and N-F sarcoma.

It is of consequence to note that none of the previously prepared placental extracts were found to possess therapeutic effects against leukemia, as shown by the description vide infra.

On the other hand, Carbazilquinone (Arakawa, M. et al Gann, 61 485, 1970), cytosine arabinoside (Talley, K. et al. Blood 21 352, 1963), Daunomycin (Tan, C. et al, cancer 20 333, 1967), Adriamycin (Di Marco, A. et al. Cancer Chemotherapy reports 53 33, 1969), L-asparaginase (Kidd, G. G. et al. Journal of Experimental Medicine 98 565, 1953) are among known anti-leukemic agents. These materials are extracted from natural sources, however, other than the placenta, or they have been chemically synthesized. However, all the anti-leukemic agents, so far known and used, are not specific in effect to the leukemic cells, but are observed clinically to give rise to various undesirable side effects, such as leucopenia, thrombocytopenia, anemia, hemorrhage, vomitting, diarrhea, fever, renal lesion, hepatic lesion, jaundice, etc. Therefore, therapeutic use of these prior art materials also required auxiliary care in order to prevent such inevitable complications. Acceptable therapeutic results have, therefore, not been fully achieved, due to the quite serious complications derived from the side effects. Chemotherapy for leukemia at the present time is therefore, only capable of leading to a remission of the disease, but this is achieved by a trade-off between longer survival and host toxicity, but complete cure has not been possible.

SUMMARY OF THE INVENTION

Under such premise that prior art anti-leukemic agents seem to lack specificity in their inhibitory effects against leukemic cells, extensive research was now conducted to seek new anti-leukemic agents. It has now been found that a specially prepared placental extract will possess excellent, anti-leukemic affects as described below without any possible side effects. The effector is hereinafter referred to as D-factor.

The methods for preparing D-factor in the present invention consists of the steps:

A. grinding the placenta with water or diluted physiological saline to form an emulsion, and adding to the emulsion mixture of aqueous acetic acid and hydrochloric acid to acidify it to 0.5 to 2.0 N;

B. heating the acidified emulsion;

C. cooling the emulsion and removing insoluble protein by centrigugation and further, after neutralizing with an alkali solution, centrifuging said emulsion to remove insoluble matter and collect a clear supernatant;

D. concentrating said supernatant, and dialyzing the resulting concentrated liquid through a dialysis membrane or filtering through a membrane filter to obtain a dialyzed fluid or filtrate;

E. subjecting the dialyzed fluid or filtrate, after concentration, to column chromatography, using Sephadex, to obtain any one of fractions, of 0.96 - 1.82 in distribution coefficient with cross-linked dextran known as Sephadex G-25, of 0.35 – 1.24 with cross-linked dextran known as Sephadex G-15, or of 0.35 – 1.25 with cross-linked dextran known as Sephadex G10, and final product; and F. lyophilizing the obtained fraction.

The properties of the Sephadex types are described in Cantow, Polymer Fractionation, Academic Press, 1967, pages 149 to 151. Sephadex G-25 has an exclusion limit of 5,000 molecular weight, G-15 of 1500 molecular weight, and G-10 of 700 molecular weight.

DETAILED DESCRIPTION OF THE PREFERRED EMBODIMENTS

Figure 1:
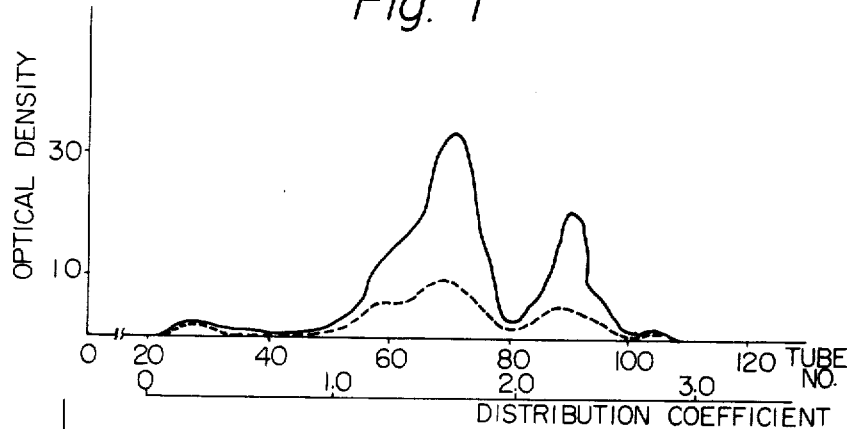
FIGS. 1 through 3 show column chromatograms of concentrated human placental extract as prepared by the present invention with Sephadex G-25, G-15 and G-10, respectively.

1. Preparation of placental emulsion and its acidification

"Placenta" refers to human placenta or a placenta of mammalian origin, such as those of bovine and swine. The placenta used herein may be fresh or frozen. The placenta is washed with an ample supply of re-distilled water. If frozen material is used, it is first thawed. Sterile water or saline solution is added to the placenta in equal amount to wet weight of the material. The placenta is then minced into pieces and ground down in a mixture of aqueous acetic acid (20 – 30%) and hydrochloric acid (1 – 20%) in the mixing ratio of 25 to 75 to 25, so that the acidity of the emulsion may range from 0.5 to 2.0 N. The acidification denatures the proteins and makes them insoluble, as well as solubilizes cytoplasm and connective tissue.

Acetic acid and hydrochloric acid should be preferably used for this purpose rather than nitric acid and sulfuric acid, because the latter two acids can cause decompositon nitration, dehydration or deamination of proteins and sugars in the emulsion, and can cause difficulties in extracting D-factor. Phosphoric acid is also not preferable because it results in not only slower extraction of D-factor but also lower activity of the factor per unit volume of purified fraction (hereinafter called extract).

The optimum range of acidity was determined empirically to be 0.5 – 2.0 N based on the following experiments of extraction efficiency and activity of the resultant D-factor.

EXPERIMENT 1

A total of 13 samples of D-factor fraction were prepared following the same procedure as that described in Example 1, below except with variation in acidity ranging from 0.1 – 2.5 N.

The extraction efficiency is computed by the following formula:

$$\text{Extraction Efficiency} = \frac{\text{dry weight of D-factor fraction}}{\text{wet weight of placenta used}} \times 100$$

The activity of D-factor fraction was bioassayed with the cell line of mouse lymphoid leukemia, L5178Y (Fischer, F. A., Annals of the New York Academy of Science 76 673, 1958). The assay systems comprise RPMI 1640 medium (NISSUI SEIYAKU) containing 10% fetal bovine serum plus every 13 series of the dried D-factor fraction to 2 mg/ml respectively. The control experiment was performed in the same fashion except that the D-factor was not contained in the medium. L5178Y cells were inoculated at the cell concentration of $1 \times 10^4$ per ml in the above medium. The culture was incubated as usual and the cell numbers were counted on the 6th day with a haemocytometer. The activity of D-factor was expressed in terms of the cell number, the higher is the expected activity of D-factor. It was observed that 1.2 N in acidity in extraction procedure resulted in the highest yield of the D-factor and the highest activity of D-factor per unit weight of the extract, even though it also results in lower extraction efficiency and lower activity. Taken both extraction efficiency and activity of D-factor a 1.2 N as 100, the extraction efficiencies and the activities of the factor were rated higher than 70 and 80, respectively when the acidities ranged between 0.5 to 2.0 N. Acidities outside the range gave lower extraction efficiency and lower activity of the factor. Beyond 2 N in acidity, hydrolysis of placental proteins is excessive and the greatest of chemical species of below 5,000 dalton is increased giving an apparently larger extraction efficiency, however, the actual activity of the D-factor was lowered. Below 0.5 N in acidity, hydrolysis did not occur effectively and accordingly the apparent yield and activity per unit weight of the extract decreased. Therefore, the acidity of the emulsion should be between 0.5 and 2.0 N, and most preferably 1.2 N.

The range of the mixing ratio of acetic acid and hydrochloric acid was determined as follows:

EXPERIMENT 2

Preparations of the extract were obtained under the same conditions as in Example 1 except the mixing ratio of acidifying agents was varied as shown in Table 1. The results are also tabulated in the same table. The mixing ratio of acetic acid and hydrochloric acid of 35 to 65, respectively, gave the best results in terms of extraction effieiency and activity of the D-factor. The higher the ratio of hydrochloric acid, the more was the extraction efficiency and the less was the activity of the D-factor. The maximum activity of the D-factor was achieved at the mixing ratio of 35 to 65. Higher or lower ratios gave lower activity. Taken the extraction efficiency and the activity ot the ratio of 35 to 65 as 100, the mixing ratio which gives rating of 70 in the extraction efficiency and of 80 in the activity of the D-factor falls into the range between 75 to 25 and 25 to 75.

Mixing ratios of acidifying agents which gives lower rating in extraction efficiency and activity is not preferable.

Thus, the mixing ratio of acetic acid and hydrochloric acid is preferably in the range between 25 to 75 and 75 to 25. The optimum is 35 to 65.

Table 1

| Acetic acid | Hydrochloric acid | Extraction efficiency (%) | Ratio of extraction efficiency | Activity of D-factor | Ratio of D-factor activity |
|---|---|---|---|---|---|
| 100 | 0 | 0.05 | 35 | $1.0 \times 10^5$ | 36 |
| 95 | 5 | 0.05 | 35 | $1.0 \times 10^5$ | 36 |
| 90 | 10 | 0.05 | 35 | $1.0 \times 10^5$ | 36 |
| 85 | 15 | 0.07 | 50 | $7.5 \times 10^4$ | 48 |
| 80 | 20 | 0.07 | 50 | $6.0 \times 10^4$ | 60 |
| 75 | 25 | 0.10 | 71 | $4.5 \times 10^4$ | 80 |
| 70 | 30 | 0.11 | 78 | $4.5 \times 10^4$ | 80 |
| 65 | 35 | 0.13 | 92 | $4.3 \times 10^4$ | 83 |
| 60 | 40 | 0.13 | 92 | $4.2 \times 10^4$ | 85 |
| 55 | 45 | 0.13 | 92 | $4.2 \times 10^4$ | 85 |
| 50 | 50 | 0.13 | 92 | $4.3 \times 10^4$ | 83 |
| 45 | 55 | 0.13 | 92 | $3.9 \times 10^4$ | 92 |
| 40 | 60 | 0.14 | 100 | $3.8 \times 10^4$ | 94 |
| 35 | 65 | 0.14 | 100 | $3.6 \times 10^4$ | 100 |
| 30 | 70 | 0.14 | 100 | $4.0 \times 10^4$ | 90 |
| 25 | 75 | 0.14 | 100 | $4.0 \times 10^4$ | 90 |
| 20 | 80 | 0.15 | 107 | $5.5 \times 10^4$ | 65 |
| 15 | 85 | 0.15 | 107 | $6.0 \times 10^4$ | 60 |
| 10 | 90 | 0.15 | 107 | $1.0 \times 10^5$ | 36 |
| 5 | 95 | 0.15 | 107 | $1.0 \times 10^5$ | 36 |
| 0 | 100 | 0.15 | 107 | $1.2 \times 10^5$ | 30 |
| Control experiment (medium not contained D-factor) | | | | $8.5 \times 10^5$ | — |

2. Heating

The acidified emulsion is heated to denature placental proteins, and to solubilize the cytoplasm and the connective tissue. Heating at higher temperatures and for longer periods of time may extend decomposition of placenta to yield more chemical species of low molecular weight which, in turn, increases extractable substances but decreases the activity of D-factor per weight of the extract.

The following experiment was carried out in order to determine the optimum conditions of heating A total of 9 preparations of placental extract were obtained following the same procedure as described in Example 1 below, except with variation in temperature of heating ranging between 55° and 95° C by every 5° C increment with duration of heating held for 40 min. The extraction efficiency and the activity of D-factor of each preparation were evaluated in the same fashion as that in EXPERIMENT 1. Results are tabulated in Table 2. The combination of heating conditions, namely, 80° C and 40 min., gave the best result in extraction efficiency and the activity of D-factor. Taken the extraction efficiency and the activity of D-factor at 80° C, 40 min. as 100, the combinations of temperatures between 75° and 90° C and duration of heating, 40 min., provided better than 70 in extraction efficiency and more than 80 for the activity of D-factor. Heating other than at the temperatures between 75° and 90° C resulted in less favorable ratings of both parameters.

Table 2

| Heated temperature | Extraction efficiency (%) | Ratio of extraction efficiency | Activity of D-factor | Ratio of D-factor activity |
|---|---|---|---|---|
| 55 | 0.02 | 15 | $5.0 \times 10^4$ | 70 |
| 60 | 0.02 | 15 | $5.0 \times 10^4$ | 70 |
| 65 | 0.04 | 30 | $4.1 \times 10^4$ | 85 |
| 70 | 0.08 | 60 | $4.2 \times 10^4$ | 83 |
| 75 | 0.12 | 92 | $3.8 \times 10^4$ | 92 |
| 80 | 0.13 | 100 | $3.5 \times 10^4$ | 100 |
| 85 | 0.14 | 107 | $3.8 \times 10^4$ | 92 |
| 90 | 0.15 | 115 | $4.3 \times 10^4$ | 81 |
| 95 | 0.18 | 138 | $4.7 \times 10^4$ | 74 |
| Control experiment (medium not contained D-factor) | | | $8.7 \times 10^5$ | — |

Next a total of 7 preparations of extract were obtained in the same procedure as described in Example 1 with heating temperature kept at 80° C, except with variation in duration of heating ranging between 10 and 70 min. in 10 min. increments. The extraction efficiency and the activity of D-factor were evaluated following the same procedure as described above. The results are tabulated in Table 3.

Table 3

| Time of heating (min.) | Extraction efficiency (%) | Ratio of extraction efficiency | Activity of D-factor | Ratio of D-factor activity |
|---|---|---|---|---|
| 10 | 0.01 | 7 | $1.0 \times 10^5$ | 35 |
| 20 | 0.05 | 36 | $5.0 \times 10^4$ | 70 |
| 30 | 0.12 | 86 | $3.8 \times 10^4$ | 92 |
| 40 | 0.14 | 100 | $3.5 \times 10^4$ | 100 |
| 50 | 0.15 | 107 | $3.6 \times 10^4$ | 97 |
| 60 | 0.15 | 107 | $3.6 \times 10^4$ | 97 |
| 70 | 0.17 | 121 | $4.5 \times 10^4$ | 77 |
| Control experiment (medium not contained D-factor) | | | $8.6 \times 10^5$ | — |

It is indicated that the combination of heating conditions, 80° C and 40 min., gave the best result in the extraction and the activity of D-factor.

Taken the extraction efficiency and the activity of D-factor at the above optimum conditions as 100, combinations of heating ranging between 30 and 60 min. at 80° C, gave, a rating of more than 70 for extraction efficiency and more than 80 for activity of D-factor. Heating conditions other than those described above were not favorable.

3. Removal of proteinous substance and pH adjustment

A portion of the placental proteins is insolubilized by acid heating. The insoluble proteinous substance was removed by centrifugation. The pH of the supernatant is adjusted to neutrality with an alkaline solution, preferably aqueous sodium hydroxide or potassium hydroxide. Maximum removal of proteinous substance could be achieved by centrifugation when the solution was acidified, because some proteins are solubilized neutralization, which retards removal of protein. On neutralization of the supernatant, some insolubles may precipitate out, and if so, they should be removed.

In general, extracts from living matter should be autoclaved in order to inactivateany pathogens continued therein, such as viruses. It is thus, desireable to autoclave after neutralization. The D-factor is so heat-stable that the extract can be sterilized at 110° C, 15 min. or 120° C, 10 min. under steam pressure of 1.0 – 1.5 Kg/cm², which are the same conditions as are used for sterilizing a microbial culture medium.

4. Concentration; Dialysis or Filtration

After autoclaving the preparation is centrifuged so as to remove any resultant insoluble substances, and the supernatant is collected. If the autoclaving step is omitted there is not need to clarify the solution a second time. The clear solution is concentrated up to 1/10 to 1/30 the volume of the original solution, under reduced pressure.

The concentrate is dialysed against triply distilled water by ordinary procedures, or is filtered through a membrane-filter, in order to remove any chemical species of high molecular weight. Dialysis of the concentrate is carried out in an ordinary cellulose tubing, and the dialyzed fluid is collected. Filtration of the concentrate is carried out through a membrane filter, e.g. Sartorius membrane filter (Sartorius Co) or Holo-fibre 50 (Dow Chemical Co.), and the filtrate is to be collected.

5. Concentration and Chromatography by means of Sephadex

The dialyzed fluid or the filtrate are concentrated to 1/100 - 1/200 or to 1/5 - 1/10 the volume of the original solution under reduced pressure, respectively. The concentrate is subjected to chromatography with any one of Sephadex G-25, G-15 and G-10 to obtain a fraction containing D-factor. The Sephadex column is equilibrated with diluted (1:100) phosphate buffered saline, which is free from calcium and magnesium, with triply distilled water. The concentrae is layered on the top of the column and subsequently eluted with the same buffer at the rate of 5 - 10 ml per 10 min. Any one of the fractions of 0.96 - 1.80 in distribution coefficient with Sephadex G-25, of 0.35 - 1.24 with Sephadex G-15 and of 0.35 - 1.25 with Sephadex G-10 is collected.

The size of column to be used is dependent on the volume of the concentrate, but is independent of its concentration. The size of the Sephadex column is 10 to 20 fold the volume of the concentrate in order to separate a fraction containing D-factor. The fraction as separated by means of Sephadex column chromatography is definitively specified in terms of the distribution coefficient (Kd) vide infra. The distribution coefficient (Kd) is computed by the formula:

$$Kd = \frac{Ve - Vo}{Vi} = \frac{Ve - Vo}{a\,Wr}$$

$Ve$: effluent volume run out till the solute is eluted.
$Vo$: solvent volume outside the gel particles.
$Vi$: solvent volume inside the gel particles.
$a$: a weight of dry gel particles.
$Wr$: the weight of solvent held per unit weight of dry gel particles.

The distribution coefficient is used as an index of the solute to specify its containing fraction eluted from Sephadex column, independent of the size of column and the rate of elution. (Hiroshi Moriya. "Gel Filtration Method", Hirokawa-shoten, 1971). Since the molecular weight of D-factor is relatively low, Sephadex G-25, G-15 or G-10 is used for separation. Use of Sephadex G-50, or one of higher degree of cross-linking, failed to obtain a fraction containing D-factor as described in Sephadex G-15, fractions, 1 of 0.06 - 0.34 in Kd, 2 of 0.35 - 1.25, 3 of 1.26 - 1.85 and 4 of 1.86 - 3.3 were obtained. With Sephadex G-10, fractions, 1 of 0.06 - 0.34 in Kd, 2 of 0.35 - 1.25, 3 of 1.26 - 1.85, and 4 of 1.86 -0 3.3 were obtained. The extraction efficiency and the activity of D-factor were determined with each of 12 fractions according to the procedure described in EXPERIMENT 1. Results are tabulated in Table 5.

Figure 2:
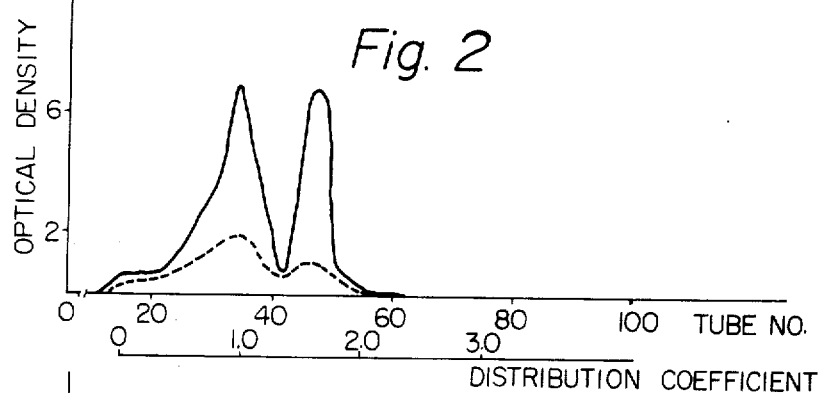
Figure 3:
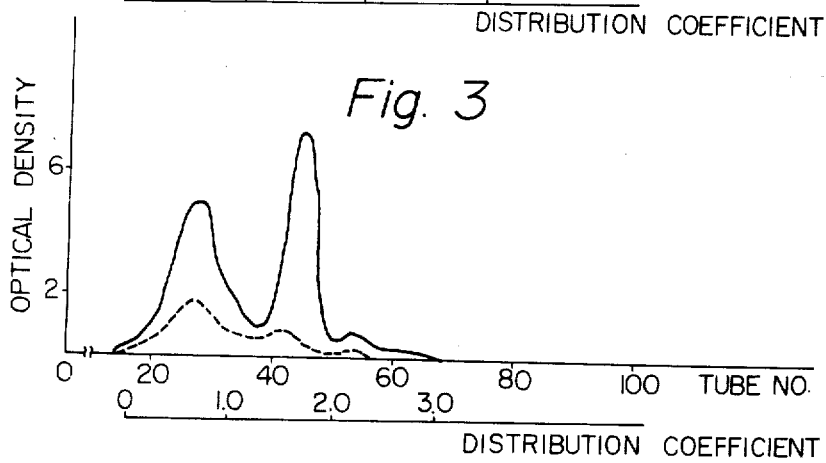
Figure 4:
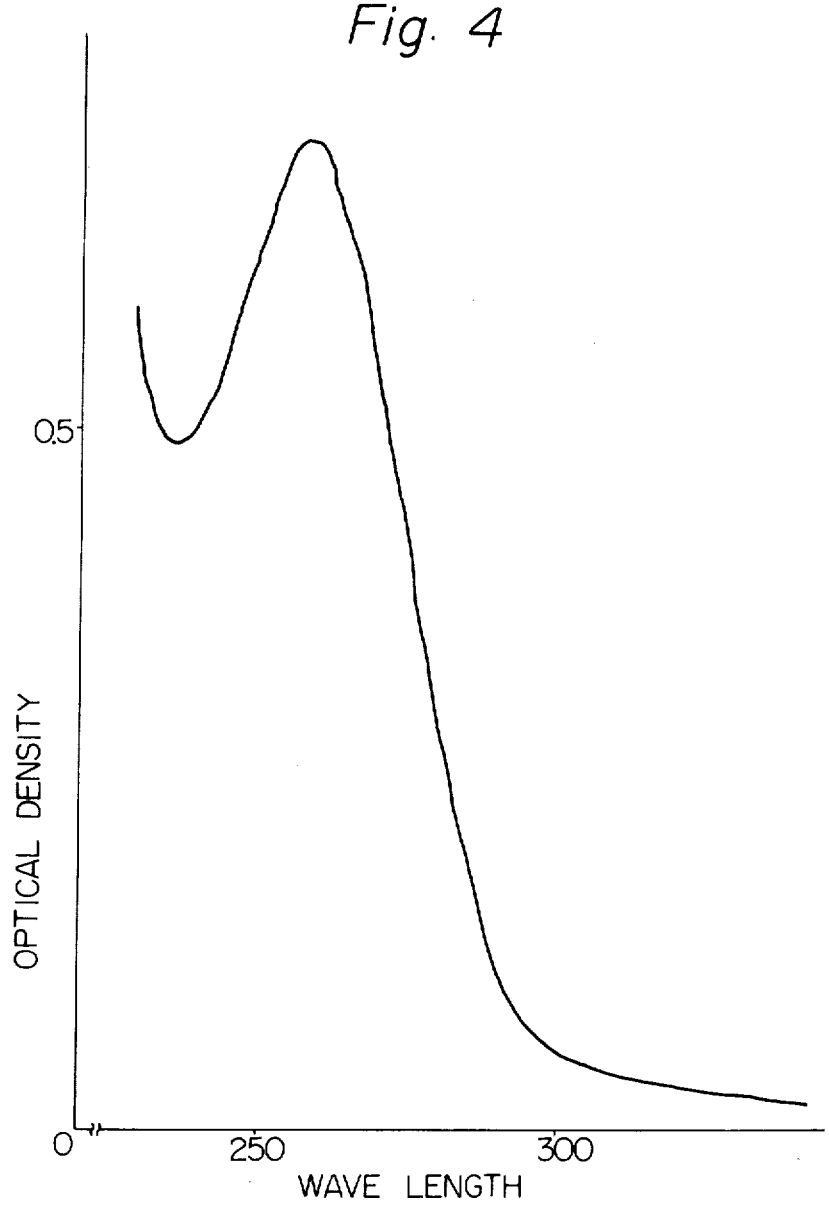
FIG. 4 illustrates the U.V. absorption spectrum of the fraction 2 which was obtained from Sephadex G-25 of the placental extract.

The accompanying FIGS. 1, 2 2 and 3 respectively show chromatograms of the placental extract with Sephadex G-25, G-15 and G-10. In each figure, abscissa represents optical densities (OD's) of the effluent and ordinate represents tube numbers and values of Kd. A solid line represents OD's at 260 nm and dotted line OD's at 280 nm. Fraction 2 at any one of Sephadex column exhibited a potent growth-inhibitory effect on the cell line of mouse lymphoid leukemia. None of the other fractions showed such effect. As shown in FIGS. 1 through 3 and Table 5, D-factor was exclusively recovered in fraction 2 at any one of Sephadex column chromatography.

Therefore, the present method can be effective in obtaining D-factor, or the fraction containing D-factor.

Some physico-chemical properties of the fraction 2 is described as follows. Absorption maximum in ultraviolet region lies at 258 nm. Molecular weight was estimated as below 5,000 dalton.

Table 4

|  | Sephadex G-25 | Sephadex G-15 | Sephadex G-10 |
| --- | --- | --- | --- |
| Weight of Sephadex (g) | 86 | 66 | 76 |
| Coloum (diameter × length) (cm) (cm) | 2.5 × 90 | 2.5 × 40 | 2.5 × 40 |
| Sample applied (ml) | 20 | 6 | 6 |
| Elute | diluted(1:100) phosphate buffered saline | diluted(1:100 phosphate buffered saline | diluted(1:100) phosphate buffered saline |
| Rate of elution (ml/10 min.) | 7 | 5 | 4.5 |
| Value of elution (ml/tube) | 7 | 5 | 4.5 |

Table 5

| | Sephadex G-25 | | | Sephadex G-15 | | | Sephadex G-10 | | |
| --- | --- | --- | --- | --- | --- | --- | --- | --- | --- |
| Fraction No. | Distribution coefficient | Extraction efficiency (%) | Activity of D-factor | Distribution coefficient | Extraction efficiency (%) | Activity of D-factor | Distribution coefficient | Extraction efficiency (%) | Activity of D-factor |
| 1 | 0.03 - 0.94 | 0.009 | $1.0 \times 10^6$ | 0.02 - 0.34 | 0.005 | $1.0 \times 10^6$ | 0.06 - 0.34 | 0.003 | $1.0 \times 10^6$ |
| 2 | 0.95 - 1.82 | 0.130 | $3.4 \times 10^4$ | 0.35 - 1.24 | 0.110 | $3.4 \times 10^4$ | 0.35 - 1.25 | 0.096 | $3.4 \times 10^4$ |
| 3 | 1.83 - 2.25 | 0.082 | $8.5 \times 10^5$ | 1.25 - 1.81 | 0.090 | $7.2 \times 10^5$ | 1.26 - 1.85 | 0.048 | $7.8 \times 10^5$ |
| 4 | 2.56 - 3.04 | 0.009 | $1.0 \times 10^6$ | 1.82 - 2.76 | 0.004 | $1.0 \times 10^6$ | 1.86 - 3.30 | 0.003 | $1.0 \times 10^6$ |
| Control experiment | | | $8.5 \times 10^5$ | | | $8.5 \times 10^5$ | | | $8.6 \times 10^5$ |

EXPERIMENT 3.

EXPERIMENT 3

Figure 5:
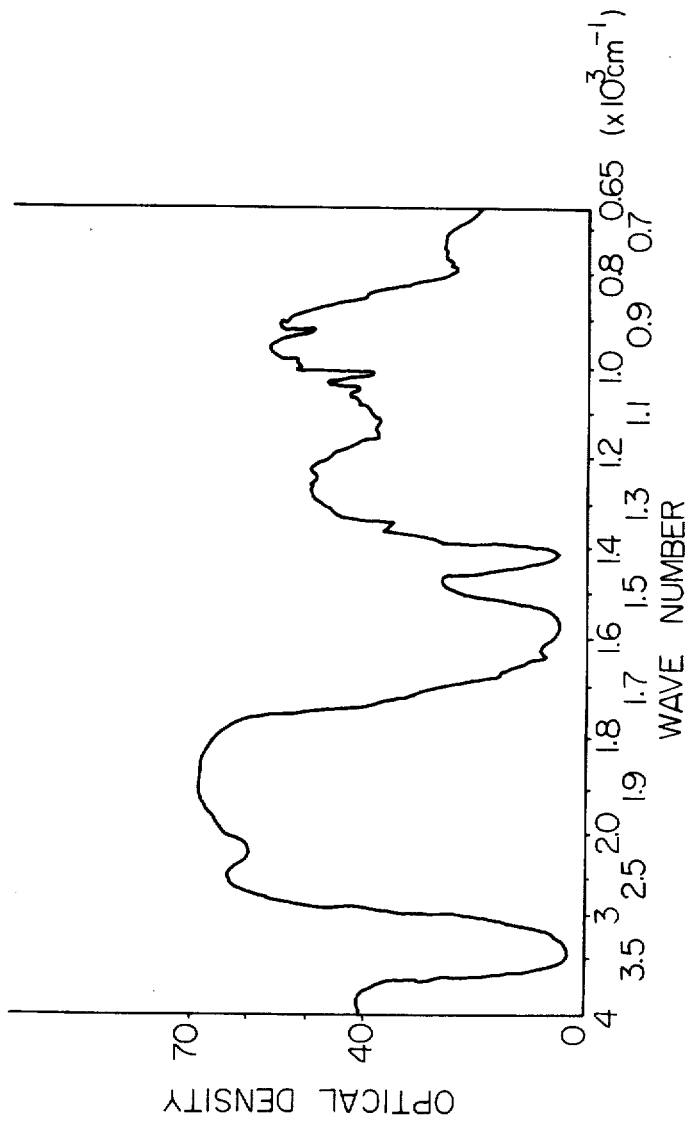
FIG. 5 illustrates infra-red absorption spectrum of the fraction 2 which was obtained from Sephadex G-25 of the placental extract.

The concentrated placental extract (total solids 20%) as prepared in Example 1 was subjected to chromatography with any one of Sephadex G-25, G-15 and G-10 under conditions shown in Table 4. Optical densities of the fractions of the eluate both at 280 and 260 nm were determined by a spectrophotometer. With Sephadex G-25, fractions, 1 of 0.03 - 0.94 in Kd, 2 of 0.95 - 1.82, 3 of 1.83 - 2.55, and 4 of 2.56 - 3.04 were obtained. With The infra-red absorption spectrum of the freeze dried preparation of fraction 2 in a KBr disk sample is shown in FIG. 5, in which peptide bonding, phosphate-ester linkage and amidoradical are noted. Accordingly, there might be nucleic acids, peptides and sugars in the extract. Other characteristics of fraction 2 as isolated by Sephadex column chromatogrphy, are summarized in Table 6.

6. Disposition of the Extract

The fraction containing D-factor (fraction 2), thus prepared, was poured into a sterilized vial after being passed through an aseptic membrane filter of below 0.2 micron in pore size, and freeze-dried.

Furthermore, the placental extracts were prepared according to the procedure of both Hieda and Boyong Ho Chin by the present inventors, the extracts were lyophilized and were examined as to this effect against leukemic cells as described in EXPERMIMENT 1. They exhibited none of growth-inhibitory effects against the malignant cells.

Next, a D-factor containing fraction, as prepared in accordance with the procedure which constitutes the present invention, was further tested as follows.

EXPERIMENT 4

Effect of D-factor on the restoration of normal function in erythroblastic leukemic cells (T-3-Cl-1) in vitro.

ml of the medium as prepared after the procedure described Example 1. A control medium was the basal medium devoid of D-factor. They were inoculated with T-3-Cl-1 cells in an ordinary fashion. Incubation of those cultures was carried out for 4 days. The activity of amino levulinic acid synthetase of the cells was determined during that period. The enzymic activity is considered to be an index of differentiation, while the reaction by the enzyme, amino levulinic acid synthetase, constitutes the rate limiting step in sequential hemoglobin synthesis.

In control culture, the enzyme activity was as low as 10.5 picomoles/30 min/mg protein. In study culture, it was 67.8 picomoles 30 min/mg protein. The result clearly showed that D-factor enhanced the enzymic activity and, in turn, caused the differentiation of the leukemic cells.

EXPERIMENT 5

Table 6

| Heads | | Sephadex G-25 | Sephadex G-15 | Sephadex G-10 |
|---|---|---|---|---|
| protein - peptide (mg/ml) | | 7.20 | 6.80 | 6.30 |
| | | acid soluble | acid soluble | acid soluble |
| (Lowry-Folin method) | | 7.19 | 6.78 | 6.26 |
| | | acid insoluble | acid insoluble | acid insoluble |
| | | 0.01 | 0.02 | 0.04 |
| Carbohydrate (mg/ml) phenol-sulfuric acid (calculated as glucose) | | 1.00 | 1.38 | 1.24 |
| Nucleic acid Ribonucleic acid (mg/ml) (Orcinol method) | | 3.12 | 3.81 | 3.56 |
| Deoxyribonucleic acid (mg/ml) (Indol method) | | 1.92 | 2.03 | 1.84 |
| Organic solvent | 70% ethanol | soluble | soluble | soluble |
| | ethylether | insoluble | insoluble | insoluble |
| | chroroform | insoluble | insoluble | insoluble |
| | aceton | insoluble | insoluble | insoluble |
| Sulfosalicylic acid reaction | | (−) | (−) | (−) |
| Biuret reaction | | (+) | (+) | (+) |
| Ninhydrin reaction | | (+) | (+) | (+) |
| Molisch test | | (+) | (+) | (+) |
| Color of powder | | light yellow | light yellow | light yellow |

Normal erythroblastic cells are capable of synthesizing hemoglobin. The established cell-line of mouse erythroblastic leukemia, T-3-Cl-1, is characteristic of its failure to synthesize hemoglobin as result of cellular dis-differentiation from erythroblastic cells. Accordingly, if the D-factor could affect the reappearance of hemoglobin synthesis in T-3-Cl-1, it would be suggestive that it can restore normal function to leukemic cells.

The strain, T-3-Cl-1, was supplied from Ikawa (Gann 57 641, 1966; ibid 58 155, 1967; Proceedings of the Japan Academy 47 220, 1971) who obtained it by the following procedure.

Friend virus (mouse leukemia virus found by C. Friend) was intraperitoneally injected into DDD mouse to form focus in its spleen. The spleen of the sacrificed animal was removed and the cells of the tissue was dispersed in a saline solution. The spleen cell suspension was injected into the mouse subcutaneously to form neoplasm. The thus, formed neoplastic cells were again intraperitoneally injected into mouse to make them ascitic form, from which a clone, T-3-Cl-1, was established in vitro. To a basal medium comprises HAM-F-12 and 20% of calf serum added was 2mg of d-factor per Animal experiment on the effect of D-factor against the leukemic cells.

In the same fashion as described in EXPERIMENT 4, T-3-Cl-1 cells were suspended in two kinds of media at the cell concentration of $5 \times 10^5$ per ml. Groups, study and control, of 10 mice each, were injected intraperitoneally with 1 ml of the suspension. The animals were fed freely dry feed (NIHON CLEA) and kept in cages at constant humidity and temperature. Survival of test animals were checked every day on both groups in order to examine the effect of D-factor. At result, survival extended to average 60 days in the study group, while average 34 days in control group. Accordingly, it was clearly demonstrated that the D-factor could antagonize against the malignancy of the leukemic cells in vivo.

EXPERIMENT 6

Effect of D-factor on the restoration of normal function in mouse lymphoid leukemic cells in vitro.

The mouse lymphoid leukemic cells, K5178Y, form a characteristic colony in the medium comprising of RPMI 1640 medium (NISSUI SEIYAKU CO.), 10% fetal bovine serum and Bacto agar (Difco Laboratories)

as do other tumor cells in general. Therefore, if the leukemic cells failed to form the characteristic colony in the mediium containing D-factor, it could be concluded with other evidences that D-factor induced the restoration of the normal function in such leukemic cells. Two kinds of study media were prepared which contained 0.5 mg and 2.0 mg of D-factor respectively in one ml of the above described soft agar medium. The control medium contained none of D-factor. Every medium was placed in five Petri dishes and cells, L5178Y, were inoculated at the cell concentration of $10^3$ in a dish. Those 15 dishes in total were incubated as usual. On the 12th day, the total colony counting was carried out with each dish. Compact and dispersed colonies were classified under a microscope of low magnification in order to examine an effect of D-factor on the restoration in L5178Y from this colony type analysis.

The term "compact" colonies refers to those in which all cells stuck together densely and the term "dispersed" colonies refers to those in which the cells in the peripheral area of a colony were dispersed in agar. The results are shown in Table 7. The total number of colony in the D-factor containing media are significantly less than those in the control medium. Also frequency of dispersed colonies in each treated medium exceeded that in the control medium. Accordingly, it was clearly shown that D-factor gave rise to normal function of lymphocyle, namely, locomotive activity in L5178Y. The D-factor does effect the restoration of normal function in the mouse lymphoid leukemic cells.

EXPERIMENT 7

The inhibitory effect of D-factor in vitro on the growtn of the mouse lymphoid leukemic cells (L5178Y) and the normal cells (C3H2K).

In this experiment, it was shown that the D-factor exercised its growth-inhibitory effect on the leukemic cells but not on the normal cells.

The L5178Y cells were inoculated at the cell concentration of $1 \times 10^4$/ml in RMPI 1640 medium supplemented with 10% fetal bovine serum of which one contained 1 mg/ml of D-factor (prepared as described in Example 2) and the other contained none of D-factor. They were incubated as usual and cell counting was carried out using a haemocytometer under a microscope on the second to eighth day in order to examine if any growth-inhibitory effect of D-factor was observed.

As the control system, the normal cells (C3H2K) which were established in vitro from normal mouse kidney were inoculated at the cell concentration of $7 \times 10^4$/ml in Eagle MEM medium (NISSUI SEIYAKU) supplemented with 10% calf serum of which one contained D-factor in 2 mg/ml and the other contained none of D-factor. The culture was incubated as usual and after detached from the bottom by trypsinization on the 1st to 7th day after inoculation as above described in order to examine the growth-inhibitory effect of D-factor on the normal cells.

Figure 6:
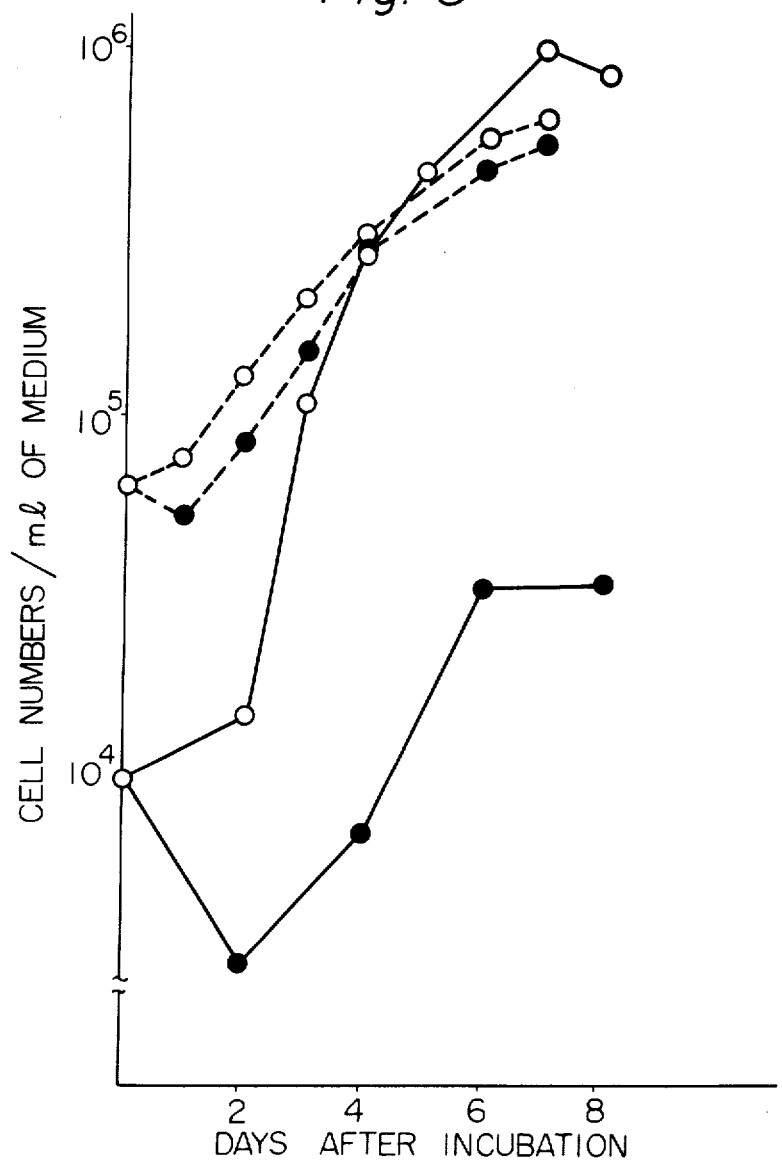
FIG. 6 illustrates the growth-inhibitory effect of D-factor both on cell line of the mouse lymphoid leukemia and that derived from normal mouse kidney.

The result is shown in FIG. 6, in which abscissa represents cell numbers per ml of the medium solution and ordinate represents culture period in days; open circle stands for control and closed circle for study groups; solid line stands for cell count of L5178Y and broken line for cell count of C3H2K.

As shown in FIG. 6, D-factor exerted specific growth-inhibitory effection the leukemic cells.

EXPERIMENT 8

The inhibitory effect of D-factor in vitro on the growth of the mouse myelogenous leukemic cells (M-1-Cl -34).

M-1-Cl -34 cells were provided by Ichikawa (Journal of Cell Physiology 74, 223, 1969), who established it as follows. Taken myleogenous cells from leukemic mouse which developed leukemia spontaneously, they were injected intravenously into normal mouse of the same strain. In two weeks, the myelogenous leukemic cells were collected from hypertrophic lymph nodes of the animal. The culture medium was prepared by dissolving 1.3 g of amino acid-vitamin medium powder (NISSUI SEIYAKU) into 1 liter of Eagle medium and adding 15% horse serum to the mixture. The myelogenous cells were inoculated at the cell concentration of $2 \times 10^7$ in the above medium in a Petri dish (d:60m/m). They were incubated as usual for 5 days with intermittent shaking. Only cells which were suspended in the medium were collected (hereinafter called M 1).

Starting with M 1 cells. M 1-Cl-34 was obtained as a clone by the soft agar methods in which double-layered EM agar medium contained 20% horse serum and 0.33% agar at the top and 0.5% at the bottom layers, was employed.

The test medium for M 1-Cl-34 ws prepared by dissolving 0.85 g of amino acid-vitamin medium powder into 1 liter of Eagle MEM and adding 10% calf serum. The M 1-Cl-34 cells were inoculated at the cell concentration of $2 \times 10^4$ per ml in the two portions of above described medium of which one contained D-factor in 2 mg/ml (which was prepared after Example 3) and the other contained none of D-factor which served as control in order to examine if any growth-inhibitory effect on the mouse myelogenous leukemic cells was observed. They were incubated as usual, cell counting was carried out on the 1st to 10th day using a haemocytometer under a microscope. The result is shown in FIG. 7, in which abscissa represents cell count per ml and ordinate represents culture period in days; open circle stands for control and closed circle for study group.

Figure 7:
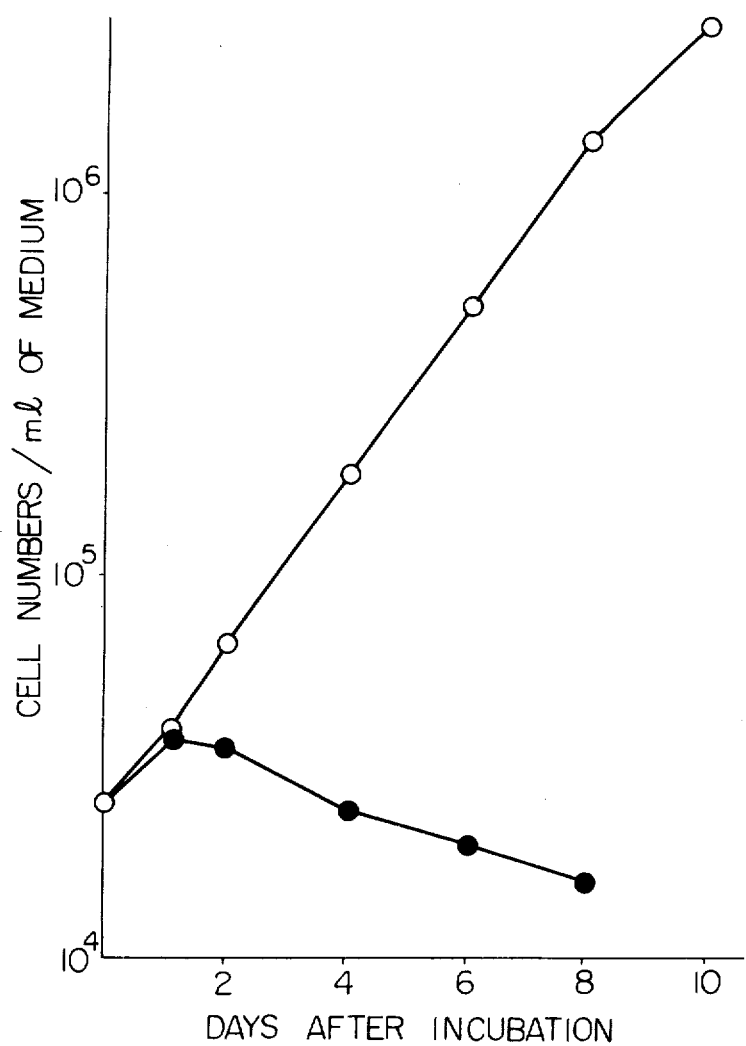
FIG. 7 illustrates the growth-inhibitory effect of D-factor on the mouse myelogenous leukemic cells.

As shown in FIG. 7, the cell number was observed to decrease since onset of the incubation indicating that M 1-cl-34 cells failed to grow in the D-factor containing medium. On the other hand, the M 1-Cl-34 cells exhibited active growth in the D-factor free medium. Accordingly, it is evident that the D-factor is capable of inhibiting the growth of myelogenous leukemic cells.

Having generally described the invention, a more complete understanding can be obtained by reference to certain specific examples, which are included for purposes of illustration only and are not intended to be limiting unless otherwise specified.

EXAMPLE 1

Four hundred grams of human placenta was washed with ample redistilled water, minced into pieces and ground with 500 ml of the water into an emulsion. Added to the emulsion was a mixture of 20% acetic acid and 10% hydrochloric acid in the ratio of 35 to 65 to 1.2 N in its acidity. The acidified emulsion was heated at 80° C for 40 min. and, after cooling, spun down at 3,000 r.p.m. for 20 min. to collect the supernatant. The collected supernatant was autoclaved at 100° C for 20 min. after pH was adjusted to 7 with 1N NaOH and after being cooled, spun down at 10,000 r.p.m. for 30 min. to remove any insoluble matter. The supernatant was concentrated to 1/20 in volume in vacuo and was subjected to dialysis in cellulose tubing (Visking Co.) against triply distilled water of 10 times the volume of the concentrate. Dialysis was repeated twice, and the dialyzed concentrate collected. The dialyzed fluid was concentrated to 1/200 in volume in vacuo and was subjected to the column (2.5 × 90 cm) chromatography with Sephadex G-25 in which the column was eluted with diluted (1:100) phosphate buffered saline, which if free from calcium and magnesium at the rate of 7 ml per 12 min. The fraction was lyophilized to yield about 450 mg of light yellow powder of D-factor.

Table 7

| Classification | Concentration of D-factor | Numbers of colonies | | |
|---|---|---|---|---|
| | | Total No. | No. of compact colonies | No. of dispersed colonies |
| Control experiment | 0 | 52 | 52 | 0 |
| | | 57 | 37 | 0 |
| | | 48 | 47 | 1 |
| | | 44 | 43 | 1 |
| | | 45 | 45 | 0 |
| | | av. 49.2 | av. 44.8 | av. 0.4 |
| Experiment (D-factor contained medium) | 0.5mg/ml | 25 | 23 | 2 |
| | | 43 | 27 | 16 |
| | | 36 | 28 | 8 |
| | | 30 | 24 | 6 |
| | | 37 | 33 | 4 |
| | | av. 34.2 | av. 27.0 | av. 7.2 |
| | 2.0mg/ml | 1 | 0 | 1 |
| | | 3 | 0 | 3 |
| | | 2 | 2 | 0 |
| | | 3 | 1 | 2 |
| | | 1 | 1 | 0 |
| | | av. 2.0 | av. 0.8 | av. 1.2 |

EXAMPLE 2

Three hundred grams of human placenta was washed with ample redistilled water, minced into pieces, added with 400 ml of diluted (1:100) saline and ground down to an emulsion. Added to the emulsion was a mixture of 20% acetic acid and 15% of hydrochloric acid in the ratio of 50 to 50 to 1N in acidity. The acidified emulsion was heated at 75° C for 60 min. and, after cooled, spun down at 3,000 r.p.m. for 20 min. to collect the supernatant. The collected supernatant was autoclaved at 120° C for 10 min. and, after cooled, spundown at 5,000 r.p.m. for 30 min. to remove any insoluble matter. The supernatant was concentrated to 1/10 in volume in vacuo and was subjected to filtration under reduced pressure with Sartorious membrane filter (Sartorious Company) to collect the filtrate. The filtrate, after concentrated to 1/10 in volume in vacuo was subjected to column (2.5 × 40 cm) chromatography with Sephadex G-15 in which the column was eluted with the same buffer as that in Example 1 at the rate of 5 ml per 10 min. The fraction of 0.35 - 1.24 in distribution coefficient was collected. It was lyophilized to yield about 300 mg of light yellow powder of D-factor.

EXAMPLE 3

Five hundred grams of frozen bovine placenta was thawed, washed with ample re-distilled water, minced into pieces and ground down with 500 ml of re-distilled water to an emulsion. Added to the emulsion was a mixture of 25% acetic acid and 15% hydrochloric acid in the ratio of 70 to 30 to 1.2 N in its acidity. The acidified emulsion was heated at 80° C for 40 min. and, after cooled, spun down at 3,000 r.p.m. for 30 min. to collect the supernatant. The supernatant, after neutralized with 2N NaOH to pH 6.5, was autoclaved at 110° C for 15 min. to remove any insoluble matter. The supernatant, after concentrated to 1/20 in volume in vacuo, was filtered through Holofibre 50 (Dow Chemical Co.) to collect the filtrate. The filtrate, after concentrated to 1/10 in volume in vacou, was subjected to column (2.5 × 40 cm) chromatography with Sephadex G-10 in which the column was eluted with the same buffer as in Example 1 at the rate of 4.5 ml per 10 min. The fraction of 0.35 - 1.25 was collected and lyophilized to obtain about 500 mg of light yellow powder of D-factor.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for preparing a therapeutic agent which comprises:
    A. 1. mincing and grinding placenta with water or diluted physiological saline solution to form an emulsion and
    A. 2. acidifying the emulsion with a mixture of aqueous acetic and hydrochloric acid to 0.5 - 2.0 N;
    B. heating the acidified emulsion to 75°- 90° C for 30 - 60 minutes so as to insolubilize a portion of the placental proteins;
    C. 1. after cooling, centrifuging the acidified emulsion of (B) to remove the insolubilized portion and to produce a supernatant,
    C. 2. neutralizing the supernatant with an alkaline solution and
    C 3. centrifuging the neutralized supernatant so as to form a supernatant fluid and an insoluble precipitant;
    D. 1. concentrating the supernatant fluid of (C) 3 to 1/10–1/30 that of its volume under reduced pressure,
    D. 2. dialysing the concentrated fluid with cellulose tubing so as to obtain a dialysate or filtering the concentrated fluid through a membrane filter so as to obtain a filtrate and
    D. 3 concentrating the dialysate or filtrate to 1/100 to 1/200 or 1/5 to 1/10 respectively of its original volume under reduced pressure;
    E. 1. chromatographically absorbing the concentrated dialysate or filtrate on a column of a cross-linked dextran having an exclusion limit of 5000 molecular weight, of 1500 molecular weight or of 700 molecular weight and
    E. 2. eluting the chromatographically absorbed dialysate or filtrate so as to obtain the fraction of distribution coefficient 0.95 to 1.82 in the case of cross-linked dextran of exclusion limit 5000 molecular weight, of distribution coefficient 0.35 to 1.24 in the case of cross-linked dextran of exclusion limit 1500 molecular weight and of distribution coefficient 0.35 to 1.25 in the case of cross-linked dextran of 700 molecular weight; and
    F. lyophilizing said fraction.

2. The process of claim 1, wherein, in step A, the acid mixture is a mixture of 10 to 30% solution of acetic acid and 10 to 20% solution of hydrochloric acid in the ratio of 25 : 75 to 75 : 25.

3. A therapeutic agent for the treatment of leukemic cells selected from the group consisting of myelogenous leukemic cells, lymphoid leukemic cells and erythroblastic leukemic cells prepared by the process of claim 1.

* * * * *